United States Patent [19]
Davidson et al.

[11] Patent Number: 4,595,759
[45] Date of Patent: Jun. 17, 1986

[54] CYCLOHEXANE CARBOXYLIC ACIDS AND DERIVATIVES THEREOF AS ANTIDYSRHYTHMIC AGENTS

[75] Inventors: Thomas A. Davidson, Penfield; Telfer L. Thomas, Pittsford, both of N.Y.

[73] Assignee: Pennwalt Corporation, Philadelphia, Pa.

[21] Appl. No.: 701,797

[22] Filed: Feb. 15, 1985

Related U.S. Application Data

[63] Continuation of Ser. No. 524,701, Aug. 19, 1983.

[51] Int. Cl.$^4$ ............... C07D 211/06; C07C 121/66; C07C 103/85
[52] U.S. Cl. .................................. 546/234; 546/239; 560/37; 560/42; 560/45; 560/48; 562/442; 562/451; 562/452; 562/457; 564/164; 564/165; 558/426
[58] Field of Search ............... 560/37, 42, 45, 48; 562/452, 457

[56] References Cited

U.S. PATENT DOCUMENTS 3,530,126  9/1970  Bernasconi et al. ............ 546/230
3,557,127  1/1971  Satzinger ............ 546/230

FOREIGN PATENT DOCUMENTS 230351 12/1963 Austria .

OTHER PUBLICATIONS

Borch et al, *J. Am. Chem. Soc.*, vol. 93, pp. 2897–2904, (1971).
Lane, *Aldrichimicas Acta*, vol. 8, No. 1, pp. 3–10, (1975).

*Primary Examiner*—Natalie Trousof
*Assistant Examiner*—Bruce D. Gray

[57]     ABSTRACT

The 2-aryl-1-aminoalkylcyclohexane nitrile, carboxylic acid or amide and derivatives thereof and methods of preparing same.

23 Claims, No Drawings

CYCLOHEXANE CARBOXYLIC ACIDS AND DERIVATIVES THEREOF AS ANTIDYSRHYTHMIC AGENTS

This application is a continuation of application Ser. No. 524,701 filed Aug. 19, 1983.

INTRODUCTION AND BACKGROUND

The present invention provides a novel class of cyclohexane nitriles and carboxylic acids, and amides and esters thereof that are useful as antidysrhythmic agents. While the art teaches cyclohexane compounds structurally related, as in U.S. Pat. No. 3,974,157 and British Pat. No. 615,136, neither teaches an analogue bearing a carboxyl, carboxyester, amide or nitrile group on the number one carbon of the cyclohexane ring.

THE INVENTION

The present invention pertains to new cyclohexane compounds of the formula:

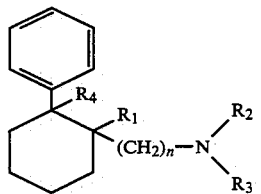

wherein $R_1$ is from the class of cyano, carboxyl, allkylcarboxylate, carboxamido, N-alkyl carboxamido and N,N-dialkylcarboxamido, $R_2$ and $R_3$ are from the class of hydrogen, cycloalkyl and lower alkyl with the proviso that such alkyl groups may be linked to form a heterocyclic ring with the nitrogen, $R_4$ is from the class of hydrogen and hydroxyl and n is a small whole number. The formula is intended to represent the racemic, optionally active and stereoisomeric forms, all of which are comprehended with the present invention.

Being organic bases, these compounds readily form salts with organic and inorganic acids such as hydrochloric, sulfuric, maleic, tartaric, and other non-toxic acids to form pharmaceutically acceptable acid addition salts.

The esters of these compounds in particular are effective at a relatively low dosage level in the prevention of the onset of arrhythmias and also in the reversal of arrhythmias in warm blooded animals and thus possess activity useful for the treatment of cardiac arrhythmias in humans.

A particularly satisfactory compound is that of the formula broadly represented structurally above in which $R_1$ is lower alkylcarboxylate, $R_2$ and $R_3$ are hydrogen or lower alkyl, $R_4$ is hydroxyl and n is less than about 5.

PROCESSES FOR PRODUCTION

The compounds of this invention can be prepared in several ways, and the following schemes, A, B, and C, and Examples, represent the processes illustrated in the present application, the term "ac" representing lower alkyl carboxylate.

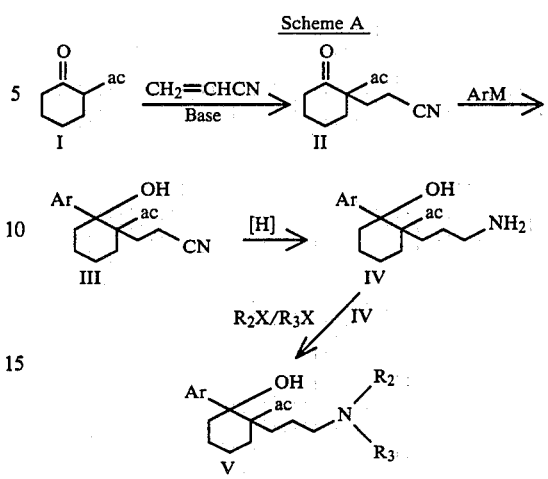

In Scheme A, ethyl 2-oxocyclohexanecarboxylate (I) can be condensed with acrylonitrile in the presence of base to form ethyl 1-(2-cyanoethyl)-2-oxocyclohexanecarboxylate (II). Treatment of this ester with an aryl magnesium halide or an aryl lithium yields the corresponding ethyl 2-aryl-1-(2-cyanoethyl-2-hydroxycyclohexanecarboxylate (III). This nitrile can be reduced to the 3-aminopropyl derivative (IV) which in turn can be alkylated to the substituted-amino derivative (V) with an alkyl halide or according to the Eschweiler-Clarke reaction with formaldehyde/formic acid to give V.

In Scheme B, below, the keto-ester (I) is reacted with allyl bromide in the presence of a base such as sodium hydride or lithium dicyclohexylamide to yield the allyl derivative (VI) which can in turn be reacted with an aryl Grignard or aryl lithium derivative to form the ethyl 1-allyl-2-aryl-2-hydroxycyclohexane-carboxylate (VII). Treatment of this olefin with borane in THF followed by iodine in the presence of sodium methoxide affords the 3-iodopropyl derivative (VIII) which can then be aminated with an amine such as dimethylamine to give, as shown below, the same ester V obtained in scheme A.

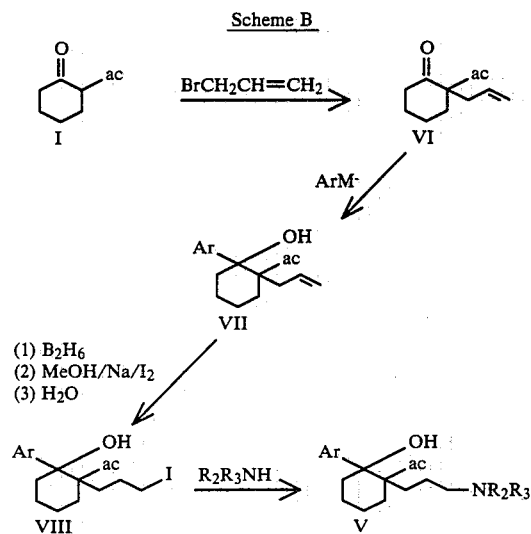

Scheme C, set forth below, is used in preparing the compounds of Examples 4 to 6 incl., in which R4 is hydrogen.

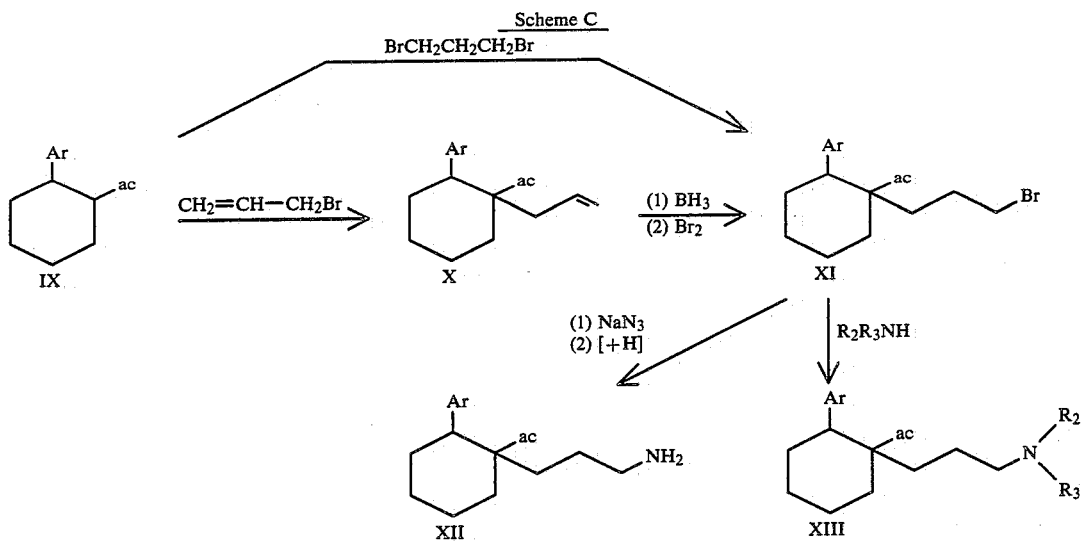

In Scheme C the 2-phenylcyclohexane carboxylic acid ester (IX) is reacted with allyl bromide in the presence of a base such as lithium diisopropylamide to yield the allyl derivative (X) which is treated with borane and then bromine to give the 3-bromopropyl derivative (XI). Alternatively (XI) is obtained from (IX) directly by alkylation with 1,3-dibromopropane. The bromide (XI) on treatment with sodium azide followed by catalytic hydrogenation affords the primary amine (XII). Secondary and tertiary amines (XIII) can be obtained by direct amination of the bromide (XI) with the appropriate amine, $R_2R_3NH$.

The invention is more specifically illustrated by the following examples which are understood to be only representative of the invention and intended in no way to limit the scope of the invention.

EXAMPLE 1

Ethyl 1-(3-aminopropyl)-2-hydroxy-2-phenylcyclohexanecarboxylate

A solution of 0.393 mole phenyl magnesium bromide in 400 ml Et₂O was added dropwise to a −40° solution of 86 gm of ethyl 1-(2-cyanoethyl)-2-oxocyclohexanecarboxylate in 450 ml Et₂O. The reaction mixture was then stirred without cooling to a temperature of ca. 3° and 60 ml saturated aq. NH₄Cl was added. After a few minutes dilute HCl was added to a pH of ca. 1, the Et₂O later was separated and the aqueous layer extracted twice more with Et₂O. The combined Et₂O extracts were washed with dilute NaOH, dried, and the solvent removed on a rotovap to give the cyanoethyl derivative which can be used directly in the next step. wt.=104 g. The cyanoester (10.6 gm) in 30 ml THF was added to 118 ml 1M.BH₃ in THF and the solution was refluxed for 20 hours. The reaction mixture was allowed to cool, then the excess BH₃ was decomposed with 35 ml conc. HCl. The THF was removed on a rotary evaporator and the residue was dissolved in water. The aqueous solution was extracted twice with Et₂O, then it was basified and the product taken up in CHCl₃. After drying over MgSO₄ and removing the solvent 4.6 gm crude product was obtained. Recrystallization from 10 ml i-PrOH yielded 2.1 gm product melting at 130°–133°.

EXAMPLE 2

Ethyl 1-(3-dimethylaminopropyl)-2-hydroxy-2-phenylcyclohexanecarboxylate

The primary amine from Example 1 (12.6 gm) was added to 20 ml formic acid, then 65 ml 35% aq. formaldehyde was added and the mixture refluxed for 6 hours. The reaction mixture was allowed to cool, added to 300 ml water, extracted with Et₂O, basified and the product was extracted into CHCl₃. The CHCl₃ solution was dried and the solvent removed in vacuo to give the desired dimethylated derivative (13.6 g) which was recrystallized from n-hexane (50 ml) to give the pure product (12.6 g) m.p. 97°–99° C.

EXAMPLE 3

1-(3-Dimethylaminopropyl)-2-hydroxy-2-phenylcyclohexanecarboxylic Acid

The ester from Example 2 (9.6 gm) in a mixture of 135 ml n-BuOH and 45 ml 45% KOH (aq) was refluxed with good stirring for 75 min., allowed to cool, and acidified with 68 ml conc. HCl. The reaction mixture was transferred to a 1 liter round bottom flask, rinsing and diluting with 40 ml n-BuOH. The mixture was concentrated to about 350 ml, cooled, and the KCl filtered off. The filtrate was concentrated to dryness then warmed and shaken with 40 ml acetonitrile, filtered and rinsed with acetonitrile (5 ml). The filtrate was cooled, seeded and the product allowed to crystallize. Wgt.=4.1 gm, m.p.=144°–145°. A second crop was obtained from the filtrate, Wgt.=1.1 gm.

EXAMPLE 4

1-(3-Aminopropyl)-2-phenylcyclohexanecarboxylic acid ethyl ester

A 5-liter 3 neck flask is fitted with a dry ice condenser and mechanical stirrer. Ammonia (3-liters) is condensed at −78° C. into the flask. Under a nitrogen atmosphere a solution of 162.0 g (81.8 mmol) of 2-biphenyl carboxylic acid dissolved in 300 ml absolute ethanol is added slowly. Sodium (60.0 g, 3 eq) is added in small portions over the course of one hour. After a further 3 hours, solid ammonium chloride (500 g) is added to the dark blue solution and the ammonia is allowed to evaporate overnight. Water (500 ml) is then added and the contents washed with 2×500 ml Et$_2$O. The aqueous phase is acidified with conc HCl and extracted with 3×500 ml Et$_2$O. The combined ether extracts are dried over MgSO$_4$ and concentrated in vacuo to afford 156.8 g of the diene acid.

The diene acid (16.8 g, 84 mmol) is thereafter dissolved in 100 ml benzene. At RT while stirring is slowly added 11.8 g (1.1 eq) oxalyl chloride. The reaction is stirred under N$_2$ for 4 hours. The contents are concentrated in vacuo to afford 20.2 g crude acid chloride. This is dissolved in CH$_2$Cl$_2$ to which 15 ml abs EtOH (excess) is added and stirred overnight. The reaction mixture is washed with H$_2$O. The organic phase is dried over MgSO$_4$, filtered and concentrated in vacuo to afford 18.73 g crude ester which is used without further purification.

The above ester (18.73 g) is dissolved in 150 ml absolute EtOH to which is added 1 g 10% Pd/C. The mixture is agitated under H$_2$ until the required uptake of H$_2$ is attained. The solution is filtered through Celite and concentrated in vacuo to afford after distillation at 125°–129°/0.3 mm 18.62 g (96% overall) of the saturated ester.

A 250 ml flask cooled to 0° under N$_2$ was charged with 60 ml THF and 5.56 g (55 mmol, 1.1 eq) of diisopropylamine. Upon addition of 39.0 ml (1.55M, 1.1 eq) of n-BuLi, the solution was stirred at 0° for 15 min. and then cooled to −78°. 2-Phenyl cyclohexane carboxylic acid ethyl ester, [11.6 g, 50 mmol] dissolved in 30 ml THF was added dropwise to the lithium diisopropylamide solution. Stirring was continued at −78° for 30 minutes and then for another 30 minutes at 0°. Upon cooling to −78°, allylbromide (6.7 g, 55 mmol, 1.1 eq) was added to the flask. The solution was stirred at −78° for 30 min. then allowed to stir at RT overnight.

The solution was then added to 100 ml H$_2$O and extracted with 2×100 ml Et$_2$O. The combined organic extracts were washed with brine and dried over MgSO$_4$. The organic material was filtered and concentrated in vacuo to afford 14.13 g of a mobile oil. Distillation (137°–140°/0.3 mm) provided 11.10 g (82%) of 2-phenyl-1-(2-propenyl)-cyclohexane carboxylic acid ethyl ester.

The 2-phenyl-1-(2-propenyl)-cyclohexanecarboxylic acid ethyl ester (4.08 g, 15 mmol) was dissolved in THF (10 ml) and cooled to 0°, under nitrogen. Upon addition of 5.2 ml of 1M BH$_3$-THF, the solution was stirred at 0° for 30 min. then at RT for 30 min. The flask was cooled to 0° and 0.5 ml MeOH was added to destroy any excess hydride. Bromine (1 ml, 20 mmol) was added dropwise followed by the addition of 30 mmol of freshly prepared NaOMe (0.7 g Na metal/10 ml anhydrous MeOH). The color of the solution changes from bright yellow to clear. Stirring was continued for 30 min. Water (50 ml) was added and the solution was extracted with Et$_2$O (2×50 ml). The combined organic extracts were washed with brine and dried over MgSO$_4$. Filtration and concentration in vacuo of the organic material afforded 5.44 g crude. Distillation yielded 4.38 g (83%) of 1-(3-bromopropyl)-2-phenylcyclohexanecarboxylic acid ethyl ester as a yellow viscous oil.

A solution of 3.52 g (10 mmol) of the bromo ester and 1.95 g (30 mmol) NaN$_3$ in 30 ml DMF was stirred overnight at 50°. Upon cooling, the contents were poured into 100 ml H$_2$O and extracted with 2×50 ml Et$_2$O. The organic extracts were washed with brine and dried over MgSO$_4$. Filtration and concentration of the organic material provided 3.09 g crude 1-(3-azidopropyl)-2-phenylcyclohexane carboxylic acid ethyl ester. The crude azide from above (3.09 g) was dissolved in 50 ml EtOH (absolute). Lindlar catalyst (0.5 g) was added and the mixture was subjected to hydrogenation. The solution was filtered through Celite and concentrated in vacuo. The residue was dissolved in Et$_2$O. Dilute hydrochloric acid was added and the organic layer was removed. The aqueous layer was basified and extracted with Et$_2$O (2×50 ml). The organic layer was dried over MgSO$_4$, filtered, and concentrated in vacuo to afford 2.43 g crude material. Distillation (140°–143°/0.3 mm) provides 2.40 g (83%) of 1-(3-aminopropyl)-2-phenylcyclohexanecarboxylic acid ethyl ester as a colorless oil.

The 1-(3-bromopropyl)-2-phenylcyclohexanecarboxylic acid ethyl ester was also made by alkylating the 2-phenylcyclohexanecarboxylic acid ethyl ester (11.6 g, 50 mmol) with 1,3-dibromopropane (11 g, 55 mmol) and the product was obtained as a yellow viscous oil, after distillation (165°–175°/0.1 mm) wt.=7.75 g (44%).

EXAMPLE 5

1-(3-N-Methylaminopropyl)-2-phenylcyclohexane carboxylic acid ethyl ester

A mixture of 1-(3-bromopropyl)-2-phenylcyclohexane carboxylic acid ethyl ester (3.52 g, 10 mmol), potassium carbonate (4.14 g, 30 mmol), 25 ml freshly condensed monomethylamine (excess), and 50 ml CH$_3$CN was stirred overnight at RT. The contents were poured into dilute hydrochloric acid (50 ml) and then extracted with 2×50 ml Et$_2$O. The aqueous layer was basified and extracted with 2×50 ml Et$_2$O. These two fractions were dried over MgSO$_4$. Filtration and concentration in vacuo provided 2.38 g crude. Distillation (145°–150°)/0.2 mm) afforded 1.69 g of 1-(3-N-Methylaminopropyl)-2-phenylcyclohexane carboxylic acid ethyl ester as a colorless oil (55%).

EXAMPLE 6

1-(3-N,N-Dimethylaminopropyl)-2-phenylcyclohexanecarboxylic-acid ethyl ester

Using the procedure of Example 5, except dimethylamine was substituted for monomethylamine 1-(3-N,N-Dimethylaminopropyl)-2-phenylcyclohexanecarboxylic acid ethyl ester was obtained as a colorless oil after distillation (145°–152°/0.2 mm), wt.=2.38 g (75%).

EXAMPLE 7

1-(3-Dimethylaminopropyl)-2-phenylcyclohexane carbonitrile

In 250 ml THF was dissolved 2-phenylcyclohexanone (100 mmol, 17.4 g) and p-toluene sulfonylhydrazide (100 mmol, 18.6 g). The mixture was stirred overnight at RT. The THF is stripped off to afford crude hydrazone 6 (mp 95°–96° C.). To this was added 200 ml EtOH and 3 eq KCN (300 mmol, 19.5 g). The contents were heated at reflux for 24 hours at which time about 150 ml of the EtOH was removed by distillation. The residue was dissolved in H$_2$O and CH$_2$Cl$_2$. The organic phase was separated, dried over MgSO₄, filtered, and concentrated to afford after distillation (106°–109°/0.2 mm), 12.35 g (67%) of the nitrile.

In a 500 ml flask was added 0.88 g of freshly washed (with hexane) KH (2.2 eq, 22 mmoles). To this was added 100 ml THF, 50 ml DMF, and 10 mmoles of 2-phenylcyclohexane carbonitrile and the contents were heated at reflux under N₂ for 3 hours. After 3 hours, a solution of 1.5 eq of freshly distilled 3-N,N-dimethylaminopropyl chloride (9.83 g) dissolved in 25 ml THF was added dropwise and the reaction then heated at reflux overnight.

The solution was cooled and diluted with 100 ml aq. acid and washed with 2×100 ml Et₂O. The aqueous phase was basified and extracted with 2×100 ml Et₂O. The ether extracts were dried over MgSO₄, filtered, and concentrated in vacuo to afford after distillation (143°–148°/0.1 mm) 2.51 g (90%) of the amine as a clear mobile oil.

EXAMPLE 8

N-Methyl-1-(2-dimethylaminoethyl)-2-phenyl-cyclohexane carboxamide

2-Phenyl-2,5-cyclohexadiene carboxylic acid (14.6 g, 73 mmol) was dissolved in benzene (100 ml) and oxalyl chloride (11.8 g, 1.1 eq) was added slowly at RT. After 4 hours the contents were concentrated in vacuo to afford 20.2 g crude acid chloride. This was dissolved in CH₂Cl₂ to which monomethylamine (35 ml, excess) was added and the reaction was stirred overnight. The reaction mixture was washed with water and the organic phase was dried over MgSO₄, filtered and concentrated in vacuo to afford 15.31 g of amide.

Crude amide from above was dissolved in 150 ml absolute ethanol to which was added 1 g 10% Pd/C. The mixture was agitated under hydrogen. The solution was filtered through Celite and concentrated in vacuo to afford after recrystallization (ethyl acetate/hexane) 14.8 g (95% overall) of the saturated amide (mp 78°–79° C.).

In a 500 ml flask was added 1.32 g of freshly washed (with hexane) KH (3.3 eq, 33 mmol). To this was added 100 ml THF, 50 ml DMF and 10 mmol of the above amide and the contents were heated at reflux under N₂ for 3 hours. Then a solution of 1.5 eq of freshly distilled 2-N,N-dimethylaminoethyl chloride (1.60 g) dissolved in 25 ml THF was added dropwise and the mixture was heated at reflux overnight.

The solution was cooled and diluted with 100 ml aq. acid and washed with 2×100 ml Et₂O. The aqueous phase was basified and extracted with 2×100 Et₂O. The ether extracts were dried over MgSO₄, filtered, concentrated in vacuo to afford after distillation 155°–160°/0.1 mm) 2.47 g (86%) of amino-amide.

EXAMPLE 9

N-Methyl-1-(3-dimethylaminopropyl)-2-phenyl-cyclohexanecarboxamide

The procedure of Example 8 was followed except that 3-dimethylaminopropyl chloride was substituted for 2-dimethylaminoethyl chloride. Thereby 10 mmol of the amide (2.17 g) was transformed into 2.55 g (84%) of amino-amide (153°–158°/0.1 mm).

EXAMPLE 10

1-(2-Dimethylaminoethyl-2-phenylcyclohexane carboxylic acid ethyl ester

Into a 250 ml 3-neck flask was added ethyl 1-allyl-2-phenylcyclohexanecarboxylate (8.42 g, 31 mmol) dissolved in 100 ml of 20% CH₃OH/CH₂Cl₂. The contents were cooled to −78° C. at which time ozone was passed through the solution until the color of the solution turned blue. Oxygen was then bubbled through to remove excess ozone. Dimethylsulfide (5 ml) was added and the contents were allowed to stir at room temperature overnight.

The contents of the flask were removed in vacuo and 50 ml THF and 10 ml aqueous HCl (2.5N) was added. The solution was heated at reflux for 4 hours. Upon cooling, the reaction mixture was added to H₂O and extracted with Et₂O (2×100 ml). The organic fractions were dried over MgSO₄, filtered and concentrated in vacuo to afford after distillation (143°–147°/0.1 mm) 7.91 g (93%) of aldehyde.

A solution of 1.07 g (12.5 mmol) of dimethylamine hydrochloride in 15.0 ml of methanol was prepared in a 50 ml flask. Potassium hydroxide (0.2 g) was added to the stirring solution. When the pellets were completely dissolved, 2.74 g (10 mmol) of the above aldehyde was added. The resulting suspension was stirred at room temperature for 15 minutes, and then a solution of 0.24 g (3.8 mmol) of sodium cyanoborohydride in 5 ml MeOH was added dropwise. Potassium hydroxide (1 g) was then added and stirring was continued until the pellets were completely dissolved. To the solution was added 25 ml of brine and 50 ml Et₂O. The organic phase was separated and the aqueous phase was basified. The aqueous phase was extracted with 2×50 ml of Et₂O. The combined organic extracts were dried over potassium carbonate, filtered, and concentrated in vacuo to afford after distillation (126°–131°/0.2 mm) 2.34 g (77%) of the desired amine.

EXAMPLE 11

1-(2-Dimethylaminoethyl-2-phenylcyclohexane carbonitrile

A procedure was used similar to that of Scheme C except that 2-phenyl cyclohexane carbonitrile replaces 2-phenylcyclohexane carboxylic acid ethyl ester. Thereby 3.70 g (20 mmol) of nitrile produced after distillation (127°–131°/0.2 mm) 3.94 g (88%) of alkylated nitrile.

A procedure was used similar to that as described for the preparation of the aldehyde of Example 10. Thereby 3.90 g (17.3 mol) of the propenyl nitrile was converted after distillation (133°–136°/0.2 mm) to 3.76 g (96%) of the aldehyde nitrile.

The procedure as described in Example 10 was thereafter used whereby 2.13 (9.4 mmol) of the aldehyde nitrile was converted after recrystallization (ethylacetate/hexane) to 1.10 g (46%) of the desired amino nitrile.

EXAMPLE 12

1-(3-N-piperidinopropyl)-2-phenyl cyclohexane carboxylic acid ethyl ester

A mixture of 1-(3-bromopropyl)-2-phenylcyclohexane carboxylic acid ethyl ester 4.24 g, 12 mmol), 25 ml piperidine and 50 ml EtOH were heated to 60° under N2 for 24 hours. The volatile material was removed in vacuo. The residue was dissolved in CHCl3 and acidified with dilute HCl. The aqueous phase was separated, basified with dilute NaOH, and extracted with CHCl3. The organic phase was dried with K2CO3, filtered and concentrated. Upon trituration with hexane, 1.80 g (42%) of desired amine was isolated, m.p. 150°–152°.

EXAMPLE 13

1-(3-cyclohexylaminopropyl)-2-phenyl cyclohexane carboxylic acid ethyl ester

A mixture of 1-(3-bromopropyl)-2-phenyl cyclohexane carboxylic acid ethyl ester (5.11 g, 14.5 mmol), 25 ml cyclohexylamine, and 50 ml ETOH were heated at 60° under N2 for 48 hrs. The volatile material was removed in vacuo. The residue was dissolved in CHCl3 and acidified with dilute HCl. The aqueous phase was separated, basified with dilute NaOH, and extracted with CHCl3. The organic phase was dried over K2CO3, filtered and concentrated. Upon trituration with hexane 2.08 g (39%) of desired amine was isolated, m.p. 154°–156°.

Biological Results

The compounds of this invention were tested for antidysrhythmic activity. Results are reported in Table 1 below. Although the compound of Example 3 failed to show activity under test conditions, it is postulated that it is active at higher dosages. The test procedures involved antiarrhythmic evaluation in dogs including the prevention of ouabain-induced arrythmias and the reversal of ouabain-induced arrhythmias. The procedures used are described below:

(1) Prevention of ouabain-induced arrhythmias.

An anesthetized dog is prepared for recording systemic arterial blood pressure and lead II ECG. The test compound is administered five (5) minutes prior to the start of ouabain infusion (2 µg/kg/min). The amount of ouabain required to induce initial ventricular premature contractions (VPCs), consistent VPCs, and fibrillation is recorded and compared to historical control values.

(2) Reversal of ouabain-induced arrythmias.

An anesthetized dog is prepared for recording systemic arterial blood pressure and lead II ECG. After a 30 minute stabilization period, a priming dose of 50 µg/kg (iv) ouabain is given. At 15 minute intervals additional increments of 10 µg/kg ouabain are given until either ventricular tachycardia or multifocal ectopic arrhythmias are obtained. Test compound is then administered and the ECG is monitored for changes indicative of reversal of the arrhythmias.

TABLE I

| Example | Ouabain Prevention | Ouabain Reversal |
| --- | --- | --- |
| 1 | Activity at 15 mg/kg | Activity at 5, 10 mg/kg |
| 2 | (Not tested) | Activity at 15 mg/kg |

The compound can be administered orally or intravenously. For human treatment an intravenous dosage of 1 to 20 milligrams is postulated with treatment to be repeated as necessary; orally a dosage of 50 to 500 milligrams, with higher or lower dosage levels being possible depending upon the physical condition of the patient is postulated. Suggested, typical formulations are given below:

Tablet 100 mg.—active ingredient
100 mg.—micro-crystalline cellulose
0.5 mg.—magnesium stearate Capsule 100 mg.—active ingredient
100 mg.—lactose
5 mg.—starch
2 mg.—magnesium stearate Intravenous Solution q.s. 100 ml—distilled water
2.5 g.—active ingredient
0.1 g.—benzyl alcohol (preservative).

Many equivalent modifications will become apparent to those skilled in the art from a reading of the above without a departure from the inventive concept.

What is claimed is:

1. A compound of the formula:

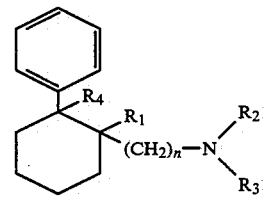

wherein $R_1$ is from the class of cyano, carboxyl, alkylcarboxylate, carboxamido, N-alkyl carboxamido and N,N-dialkylcarboxamido, $R_2$ and $R_3$ are from the class of hydrogen, cycloalkyl and lower alkyl with the proviso that such lower alkyl groups may be linked to form a heterocyclic group with the nitrogen, $R_4$ is from the class of hydrogen and hydroxyl and n is 2 or 3.

2. The compound of claim 1 wherein $R_4$ is hydroxyl.

3. The compound of claim 2 wherein $R_1$ is ethylcarboxylate.

4. The compound of claim 3 wherein n is 3, and $R_2$ and $R_3$ are hydrogen.

5. the compound of claim 3 wherein n is 3 and $R_2$ and $R_3$ are methyl.

6. The compound of claim 1 wherein $R_4$ is hydrogen.

7. The compound of claim 6 wherein n is 3 and $R_1$ is ethylcarboxylate.

8. The compound of claim 6 wherein n is 2 and $R_1$ is ethylcarboxylate.

9. The compound of claim 8 wherein $R_2$ and $R_3$ are methyl.

10. The compound of claim 7 wherein $R_2$ and $R_3$ are hydrogen.

11. The compound of claim 7 wherein $R_2$ and $R_3$ are methyl.

12. The compound of claim 7 wherein $R_2$ is hydrogen and $R_3$ is methyl.

13. The compound of claim 6 wherein n is 2 and $R_1$ is methylcarboxamide.

14. The compound of claim 13 wherein $R_2$ and $R_3$ are methyl.

15. The compound of claim 6 wherein n is 3 and $R_1$ is methylcarboxamide.

16. The compound of claim 15 wherein $R_2$ and $R_3$ are methyl.

17. The compound of claim 7 wherein $R_2$ and $R_3$ are linked to form a piperidino group with the nitrogen.

18. The compound of claim 6 wherein n is 3 and $R_1$ is dimethylcarboxamide.

19. The compound of claim 18 wherein $R_2$ and $R_3$ are linked to form a piperidino group with the nitrogen.

20. The compound of claim 6 wherein n is 3 and $R_1$ is methylcarboxylate.

21. The compound of claim 20 wherein $R_2$ is methyl and $R_3$ is methyl.

22. The compound of claim 7 wherein $R_2$ is isopropyl and $R_3$ is isopropyl.

23. The compound of claim 15 wherein $R_2$ and $R_3$ are linked to form a piperidino group with the nitrogen.

* * * * *